United States Patent [19]

Yukawa et al.

[11] 4,276,380

[45] Jun. 30, 1981

[54] PRODUCTION OF L-AMINO ACIDS

[75] Inventors: Hideaki Yukawa; Kazuoki Osumi; Terukazu Nara; Yoshihiro Takayama, all of Ami, Japan

[73] Assignee: Mitsubishi Petrochemical Co., Ltd., Tokyo, Japan

[21] Appl. No.: 120,963

[22] Filed: Feb. 13, 1980

[30] Foreign Application Priority Data

Feb. 13, 1979 [JP] Japan .................................. 54-15341
May 18, 1979 [JP] Japan .................................. 54-61109

[51] Int. Cl.$^3$ ............................................ C12P 13/08
[52] U.S. Cl. .................................... 435/115; 435/247; 435/822; 435/172
[58] Field of Search ........................................ 435/115

[56] References Cited

U.S. PATENT DOCUMENTS

| | | | |
|---|---|---|---|
| 3,907,641 | 9/1975 | Nakayama et al. | 435/115 X |
| 3,920,520 | 11/1975 | Tanaka et al. | 435/115 |

*Primary Examiner*—Lionel M. Shapiro
*Attorney, Agent, or Firm*—Sughrue, Rothwell, Mion, Zinn and Macpeak

[57] ABSTRACT

A process for producing L-valine or L-lysine which comprises aerobically culturing a bacterium belonging to the genus Acinetobacter, which utilizes ethanol and has an ability to produce and accumulate L-valine or L-lysine, in a culture medium in which ethanol is the main carbon source to produce and accumulate L-valine and/or L-lysine and collecting.

3 Claims, No Drawings

PRODUCTION OF L-AMINO ACIDS

BACKGROUND OF THE INVENTION

1. Field of the Invention

The present invention relates to a process for producing L-valine or L-lysine by fermentation. L-Valine and L-lysine are useful as essential amino acids incorporated into medicines, diets, etc. and their economical production on a commercial scale is needed.

2. Background of the Invention

Production of amino acids by the fermentation has been practiced using saccharides (carbohydrates) as the main starting materials, but it suffers from various problems such as high cost and unstable supply due to the fact that the starting materials are agricultural products, copious amounts of by-products derived from a large proportion of impurities contained in the starting material are produced, colored waste water is generated from the fermentation process, etc., and therefore fundamental improvements have been sought.

As one alternative, a process using hydrocarbons as the starting materials has been studied, but even this process has a drawback that some hydrocarbons are gaseous and some are not soluble in water, which greatly restricts their application on a commercial scale and, as a result, the yield is limited.

SUMMARY OF THE INVENTION

A principal object of the present invention is to provide an economical process for producing L-valine and L-lysine on a commercial scale.

Another object of the present invention is to provide a process of producing L-valine and L-lysine from a starting material which is readily available and inexpensive.

Another object of the present invention is to provide a process for producing L-valine and L-lysine by fermentation of ethanol.

A still further object of the present invention is to provide a bacterium of the genus Acinetobacter which is capable of producing amino acids by fermentation of ethanol.

In view of the foregoing, the present inventors have investigated using ethanol as a starting material for the production of amino acids. Ethanol is expected to be in steady supply and available cheaply and has none of the above disadvantages. As a result, certain bacteria which have an ability to produce and accumulate a remarkable amount of L-valine and/or L-lysine when cultured in a medium in which ethanol is the main carbon source have been discovered among the bacteria belonging to the genus Acinetobacter. Thus, the present invention provides a process for producing L-valine or L-lysine by aerobically culturing bacteria belonging to the genus Acinetobacter, which utilizes ethanol, and which has the ability to produce and accumulate L-valine or L-lysine in a culture medium in which ethanol is the main carbon source.

DETAILED DESCRIPTION OF THE INVENTION

The bacteria used in the present invention may be any of the naturally occurring strains, any known strains and any strains produced by the artificial mutation, belonging to the genus Acinetobacter, provided they utilize ethanol, and have the ability to produce and accumulate L-valine or L-lysine.

An example of the bacteria which produces and accumulates L-valine or L-lysine from ethanol is *Acinetobacter calcoaceticum* YK-1011 which has been deposited with the Fermentation Research Institute, the Agency of Industrial Science and Technology, Japan as FERM-P No. 4818 (deposited on Feb. 9, 1979).

This bacterium is derived and isolated from *Acinetobacter calcoaceticum* ATCC 19606 as the 5-methyl-DL-tryptophane resistant strain, and has the same characteristics as *Acinetobacter calcoaceticum* ATCC 19606 except that is is resistant to 5-methyl-DL-tryptophane.

The bacteriological characteristics of strain YK-1011 are set forth below as positive (+) and negative (−):

| | | | |
|---|---|---|---|
| Gram stain | − | Oxidation of: | |
| Acid-fast stain | − | L-Arabinose | + |
| Rod-shapes (pleomorphic) | + | D-Galactose | + |
| Spore-formation | − | Glucose | + |
| Motility | − | Lactose | + |
| Strict aerobe | + | D-Mannose | + |
| Growth at 22° | + | Rhamnose | + |
| growth at 42° | − | D-Ribose | + |
| Indole | − | D-Xylose | + |
| Hydrogen sulfide | − | D-Fructose | − |
| Voges-Proskauer test | − | Maltose | − |
| Methyl red test | − | Raffinose | − |
| Viscosity | − | D-Sorbitol | − |
| Assimilation of: | | Starch | − |
| Glucose | − | Sucrose | − |
| Sucrose | − | Nitrate reduction: | |
| Fumarate | + | in succinate-nitrate | + |
| Acetate | + | in casitone-nitrate | − |
| Citrate | + | Litmus milk: | |
| Gluconate | − | acid coagulation | + |
| Malonate | − | reduction | − |
| Succinate | + | Catalase | + |
| Glutamate | + | Urease | + |
| Aspartate | + | Phenylalanine deaminase | − |
| L-Alanine | + | Lysine decarboxylase | − |
| β-Alanine | − | Gelatinase | − |
| L-Arginine | + | Cytochrome oxidase | − |
| L-Leucine | − | Flavin pigmentation | + |
| Decane | − | Penicillin resistance (100 IU) | + |
| Tridecane | − | Growth in 5% NaCl broth | − |
| Hexadecane | − | G + C moles (%) | 42 |
| Kerosene | − | | |
| Methanol | − | | |
| Ethanol | + | | |

The method for deriving the 5-methyl-DL-tryptophane resistant strain from *Acienetobacter calcoaceticum* ATCC 19606 is explained below.

The growth of the *Acinetobacter calcoaceticum* ATCC 19606 was almost completely inhibited in a plate culture medium prepared by adding 200 μg/ml of 5-methyl-DL-tryptophane to an artificial culture medium containing 2.0 g Urea, 7.0 g ammonium sulfate, 0.5 g $KH_2PO_4$, 0.5 g $K_2HPO_4$, 0.5 g $MgSO_4.7H_2O$, 2 mg $FeSO_4.7H_2O$, 2 mg $MnSO_4.4-6H_2O$, 2 mg NaCl, 2 mg $ZnSO_4.7H_2O$, 1 liter water and 2% v/v ethanol. The derivation of its mutant was carried out by subjecting it to the nitrosoguanidine treatment (nitrosoguanidine 200 μg/ml, 30° C., 15 minutes, pH 7.0 by trismaleic acid buffer; E. A. Adelberg et al, Biochem. Biophys. Res. Comm. 18, 788 (1965)) in a known manner, culturing it on the plate culture medium containing 200 μg/ml of 5-methyl-DL-tryptophane as above at 30° C. for 3 to 5 days and isolating the colony produced. Needless to say the derivation of the mutant is not limited to the above nitrosoguanidine treatment and can be effected by ultraviolet irradiation or treatment with various chemicals.

The preferred embodiment for the practice of the present invention is described as follows.

Ethanol is used as the carbon source in the culture medium and the initial concentration is suitably chosen in a range of about 1 to 5% v/v depending on the particular strain used. With its consumption, ethanol is intermittently supplemented to give an optimum concentration (about 0.01 to 5% v/v and more preferably about 0.01 to 2% v/v) which does not inhibit the growth of the strain or the production of L-valine or L-lysine.

The nitrogen source (about 0.01 to 15% v/v) is chosen among ammonium sulfate, ammonium nitrate, ammonium phosphate, urea, etc. depending on the ability of the strain to utilize the nitrogen source. Further, depending on the bacteria necessary amounts (about 10% v/v or less) of organic nutrient sources such as amino acids (e.g., glutamic acid, alanine, glycine, etc.), corn steep liquor, bouillon, yeast extract, etc., inorganic salts (e.g., sulfates or hydrochlorides of Ca, Mg, Na, K, Fe, Ni and Co), vitamins (e.g., groups of Vitamin B, pantothenic acid, benzoic acid, etc.), etc. are added to prepare a culture medium.

The conditions for culturing are typically a temperature of about 20° to 37° C. and a pH of about 4 to 10 and preferably about 25° to 35° C. and a pH of about 6 to 8. The optimum conditions will depend on the particular strain used. Cultivation will generally take 2 to 7 days. The cultivation is conducted under aerobic conditions.

After cultivation, L-valine or L-lysine may be recovered from the liquor by known methods such as using an ion-exchange resin, activated carbon, concentration-crystallization, etc. See, for example, JIKKEN NOGEI KAGAKU (*Experimental Agricultural Chemistry*), the first volume, pages 284–285, Tokyo University, Faculty of Agriculture, Department of Agricultural Chemistry, published by Asakura Shobo (1960).

The following Examples will illustrate the invention in more detail.

The quantitative assay of L-valine or L-lysine was conducted by the microorganic analytical method using Leuconostoc Mesenteroides ATCC 8042, and the reported values are those from which the amounts of L-valine or L-lysine contained in the culture medium have been deducted.

EXAMPLE 1

10 ml of the pre-culture medium containing urea 2.0 g, ammonium sulfate 7.0 g, $KH_2PO_4$ 0.5 g, $K_2HPO_4$ 0.5 g, $MgSO_4.7H_2O$ 0.5 g, yeast extract 0.5 g, Casamino acid 0.5 g, $FeSO_4.7H_2O$ 2 mg, NaCl 2 mg, $CaCl_2.2H_2O$ 2 mg and tap water 1 liter was poured into a large test tube having an inner diameter of 24 mm, and sterilized at 120° C. for 10 minutes. 0.2 ml of ethanol was added under aseptic conditions and *Acinetobacter calcoaceticum* YK-1011 was inoculated to effect shake culture at 30° C. for 2 days. Then, 10 ml of the same culture medium as the pre-culture medium was poured into a large test tube having an inner diameter of 24 mm, sterilized at 120° C. for 10 minutes, 0.2 g of calcium carbonate which had been sterilized by dry heating was added, 0.2 ml of ethanol was added and then 0.2 ml of the pre-culture liquor was inoculated to effect shake culture at 30° C. for 7 days. Ethanol was supplemented as it was consumed. On such occasions, care was taken so that the concentration of ethanol did not exceed 3% v/v. On the 7th day after the start of cultivation, it was found that 600 mg/l of L-valine had been accumulated. 100 ml of this culture liquor was centrifuged to separate the cells, the supernatant liquid was passed through a strongly acidic cation exchange resin (Diaion SK-1B, H type) to adsorb L-valine, and 0.5 N ammonia water was passed to elute L-valine according to a known method. The fractions containing L-valine were concentrated, decolored using activated carbon and cold ethanol was added to obtain crude crystals of L-valine. The production of L-valine was not observed with *Acinetobacter calcoaceticum* ATCC 19606 similarly cultured.

EXAMPLE 2

10 ml of a pre-culture medium (urea 2.0 g, ammonium sulfate 7.0 g, $KH_2PO_4$ 0.5 g, $K_2HPO_4$ 0.5 g, $MgSO_4.7H_2O$ 0.5 g, yeast extract 0.5 g, Casamino acid 0.5 g, $FeSO_4.7H_2O$ 2 mg, $MnSO_4.4-6H_2O$ 2 mg, $ZnSO_4.7H_2O$ 2 mg, NaCl 2 mg, $CaCl_2.2H_2O$ 2 mg, biotin 200 µg, thiamine hydrochloride 100 µg and tap water 1 liter) was poured into a large test tube having an inner diameter of 24 mm, sterilized at 120° C. for 10 minutes, 0.2 ml of ethanol was added aseptically and *Acinetobacter calcoaceticum* YK-1011 was inoculated to effect shake culture at 30° C. for 2 days. Then 10 ml of the same culture medium as the pre-culture medium was poured into a large test tube having an inner diameter of 24 mm, sterilized at 120° C. for 10 minutes, 0.2 g of calcium carbonate which had been sterilized by dry heating was added, 0.2 ml of ethanol was added and then 0.2 ml of the pre-culture liquor was inoculated to conduct a shake culture at 30° C. for 7 days. Ethanol was supplemented as it was consumed. On such occasions, care was taken so that the concentration of ethanol should not exceed 3% v/v. On the seventh day after the start of the culture, the culture liquor containing L-lysine accumulated to 6 g/l was obtained.

50 ml of the collected culture liquors similarly cultivated was centrifuged to separate the cells. The supernatant liquid was passed through a strongly acidic ion exchange resin Diaion SK-1B to adsorb L-lysine. Then 5% v/v ammonia water was passed to elute the adsorbed L-lysine, the eluate was concentrated under reduced pressure. Hydrochloric acid was added to the concentrate and cooled to separate the crystals of L-lysine hydrochloride dihydrate, yield 210 mg.

While the invention has been described in detail and with reference to specific embodiments thereof, it will be apparent to one skilled in the art that various changes and modifications can be made therein without departing from the spirit and scope thereof.

What is claimed is:

1. A process for producing L-valine which comprises aerobically culturing a bacterium of the strain *Acinetobacter calcoaceticum* YK-1011, which utilizes ethanol and has an ability to produce and accumulate L-valine, in a culture medium in which ethanol is the main carbon source to produce and accumulate L-valine and collecting the L-valine.

2. The process of claim 1, wherein said bacterium is derived from *A. calcoaceticum* ATCC 19606.

3. The process of claim 2, wherein said bacterium is derived by nitrosoguanidine treatment.

* * * * *